United States Patent [19]

Backman

[11] 4,067,091

[45] Jan. 10, 1978

[54] METHOD OF PREPARING HUMAN REMAINS FOR STORAGE

[76] Inventor: Philip E. Backman, 2570 Gay St., Eugene, Oreg. 97401

[21] Appl. No.: 741,552

[22] Filed: Nov. 15, 1976

[51] Int. Cl.² .............................................. A01N 1/00
[52] U.S. Cl. ...................................................... 27/21
[58] Field of Search ...................... 27/21, 22; 128/399

[56] References Cited

U.S. PATENT DOCUMENTS 3,408,712  11/1968  Pauliukonis et al. .................... 27/22

*Primary Examiner*—John D. Yasko
*Attorney, Agent, or Firm*—James D. Givnan, Jr.

[57] ABSTRACT

A method for processing human remains consisting of the steps of sequentially subjecting same to a below-freezing environment and a cryogenic environment and thereafter reducing the solid remains to a particulate state by subjecting it to mechanical fractionating means. A subsequent step consists of subjecting the frozen particulate to a below atmospheric environment for the purpose of reducing the moisture content thereof. A final step consists of storage of the remains in containers of either a permanent or temporary nature.

1 Claim, No Drawings

METHOD OF PREPARING HUMAN REMAINS FOR STORAGE

BACKGROUND OF THE INVENTION

The present invention concerns novel processing of human remains to provide an alternative to known preservation processes.

Generally speaking, human remains are subjected to one of two types of preservation — burial of the embalmed body either in the ground or in a mausoleum or alternatively, cremation. Problems associated with such established practices include those of an ecological nature, as well as those concerning land-use. With the passage of time and predicted population trends, such problems are likely to become critical.

Beyond the foregoing drawbacks to the conventional processes of storing human remains is the additional undesirable aspect of the costs incurred thereby.

SUMMARY OF THE PRESENT INVENTION

The present invention is embodied within a method comprising a series of steps for preparing the human remains for permanent storage or alternatively, storage for a designated duration.

The present method concerns the field of cryogenics as the body is reduced during processing to a cryogenic state. A distinction should be made at this point from earlier disclosed cryogenic processing of the human body such as that process disclosed in U.S. Pat. No. 3,408,712 wherein the body is preserved intact. The present method does not comprehend such preservation of the whole body but rather includes the reduction of the remains to a fragmentary mass. Further, the preservation of body cellular structure is of no present interest.

The present method entails the reduction of the body to a particulate state devoid of substantially all moisture enabling container storage thereof at ambient temperatures. A desirable feature in common with cremation is the convenient urn or other storage of the remains. Important to the extraction of moisture from the body is the step of surface enhancement accomplished by subjecting the body, while in a cryogenic state, to physical reduction. Once surface enhancement is completed, the mass is subject to direct evaporation within an artificial environment. Accordingly, the organic remains are suitable for storage in an urn or other sealed container.

DETAILED DESCRIPTION OF THE PREFERRED EMBODIMENTS

The present method embodying the invention comprehends initial storage of the body after death at a temperature somewhat below 0° C. The temperature criteria and duration of the first step is not deemed critical but rather is primarily for purposes of body preservation in an acceptable state.

Cryogenic cooling of the body is subsequently performed which entails subjecting the intact body to a coolant such as a liquid nitrogen bath or spray thereby reducing the temperature thereof to a temperature below $-100°$ C. All body liquids are, of course, solidified with the low temperature criteria somewhat dependent upon the means selected for accomplishing the step of surface enhancement, as later described. The body, for all purposes, may be considered entirely frozen with all tissue being in a solid state.

A further step entails subjecting the intact, frozen body to fractionalizing means reducing same to a particulate state. This step may be termed surface enhancement i.e., an increase in surface area of the remains is provided. Existing mechanical means such as that used in the reduction of organic or inorganic substances may be utilized in this step. By way of example, a hammer mill may be utilized. The resulting particulate representing bodily remains is reduced to a state wherein the largest particulate does not exceed approximately 13 mm.

The mass resulting from the foregoing step is continually subjected to cryogenic temperatures until commencement of the following step.

To reach a stable condition for storage of the remains, the moisture content of the body must be reduced to approximately 5% of its original value by weight. This reduction is accomplished by a process known in other fields as freeze-drying wherein processing includes the direct evaporation of certain solids from cryogenic mass while being subjected to at least a partial vacuum. This step may utilize either of the accepted processes practiced in the treatment of organic material i.e., the gas process or the vacuum process, the details of which are common knowledge in the freeze-drying art. Basically, the frozen particulate is agitated for a period while being subjected to a subatmospheric pressure to remove at least 80% to 90% of the moisture present. The material remains a few degrees below freezing while being processed. The moisture so removed is carried off by circulating gas which passes through a cold trap with the material being discharged through vacuum preserving means.

The terminal step consists of the storage of the freeze-dried particulate within a suitable container such as a sealed urn of type used for the storage of cremated remains or, alternatively, the deposit of the freeze-dried material into a sealed, easily stored container of a less permanent nature. This last alternative permits convenient disposal of the remains after a selected period of time in any manner permitted by applicable governmental requirements.

While I have shown but one embodiment of the invention it will be apparent to those skilled in the art that the invention may be embodied still otherwise without departing from the spirit and scope of the claimed invention.

Having thus described the invention what is desired to be secured under a Letters Patent is:

1. The method of preparing human remains for storage consisting of the steps of,
    subjecting the body while intact to below-freezing temperatures to prevent deterioration,
    subjecting the intact body to a cryogenic environment thereby reducing the temperature of same to a point below $-100°$ C.,
    subjecting the intact body to mechanical fracturing to reduce same to a particulate state, and
    subjecting the particulate to a freeze-drying environment for removal of approximately 95% of its water content by direct evaporation of certain solids, and
    depositing the freeze-dried material into an individual storage container which may be sealed against ambient air.

* * * * *